(12) United States Patent
Iyer et al.

(10) Patent No.: US 7,745,653 B2
(45) Date of Patent: Jun. 29, 2010

(54) FLUOROCHEMICAL COMPOUNDS HAVING PENDENT SILYL GROUPS

(75) Inventors: Suresh Iyer, Woodbury, MN (US);
Thomas P. Klun, Lakeland, MN (US);
Oscar S. Benz, Minneapolis, MN (US);
Wayne W. Fan, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 782 days.

(21) Appl. No.: 11/683,823

(22) Filed: Mar. 8, 2007

(65) Prior Publication Data

US 2008/0220264 A1    Sep. 11, 2008

(51) Int. Cl.
C07F 7/02       (2006.01)
C07F 7/10       (2006.01)
C07F 7/18       (2006.01)

(52) U.S. Cl. .................. 556/400; 556/436; 556/445; 556/482

(58) Field of Classification Search ............. 556/400, 556/436, 445, 482
See application file for complete search history.

(56) References Cited

U.S. PATENT DOCUMENTS

| | | | |
|---|---|---|---|
| 3,250,807 A | 5/1966 | Fritz et al. | |
| 3,250,808 A | 5/1966 | Moore, Jr. et al. | |
| 3,493,424 A | 2/1970 | Mohrlok et al. | |
| 3,646,085 A * | 2/1972 | Bartlett | 556/419 |
| 3,719,698 A | 3/1973 | Tesoro et al. | |
| 3,810,874 A | 5/1974 | Mitsch et al. | |
| 4,262,072 A | 4/1981 | Wendling et al. | |
| 4,321,404 A | 3/1982 | Williams et al. | |
| 4,348,462 A | 9/1982 | Chung | |
| 4,351,736 A | 9/1982 | Steinberger et al. | |
| 4,378,250 A | 3/1983 | Treadway et al. | |
| 4,508,916 A | 4/1985 | Newell et al. | |
| 4,617,057 A * | 10/1986 | Plueddemann | 106/2 |
| 4,657,959 A * | 4/1987 | Bryan et al. | 524/266 |
| 4,781,844 A | 11/1988 | Kortmann et al. | |
| 4,866,192 A * | 9/1989 | Plueddemann et al. | 556/410 |
| 4,873,140 A | 10/1989 | McIntyre | |
| 5,073,442 A | 12/1991 | Knowlton et al. | |
| 5,399,738 A * | 3/1995 | Wolter et al. | 556/420 |
| 5,866,651 A * | 2/1999 | Moren et al. | 524/588 |
| 6,183,872 B1 | 2/2001 | Tanaka et al. | |
| 6,277,485 B1 * | 8/2001 | Invie et al. | 428/336 |
| 6,649,272 B2 * | 11/2003 | Moore et al. | 428/447 |
| 6,716,534 B2 * | 4/2004 | Moore et al. | 428/447 |
| 6,815,040 B2 * | 11/2004 | Pellerite et al. | 428/142 |
| 6,923,921 B2 | 8/2005 | Flynn et al. | |
| 6,991,826 B2 | 1/2006 | Pellerite et al. | |
| 7,094,829 B2 | 8/2006 | Audenaert et al. | |
| 7,101,618 B2 | 9/2006 | Coggio et al. | |
| 7,247,386 B2 * | 7/2007 | Hooftman et al. | 428/447 |
| 7,425,279 B2 * | 9/2008 | Cote et al. | 252/8.62 |
| 2004/0077775 A1 | 4/2004 | Audenaert et al. | |
| 2004/0253369 A1 | 12/2004 | Jallouli et al. | |
| 2005/0038150 A1 | 2/2005 | Meiners et al. | |
| 2005/0054804 A1 | 3/2005 | Dams et al. | |
| 2005/0233070 A1 | 10/2005 | Pellerite et al. | |
| 2005/0249940 A1 | 11/2005 | Klun et al. | |
| 2005/0250298 A1 | 11/2005 | Bauer | |
| 2005/0250921 A1 | 11/2005 | Qiu et al. | |
| 2006/0216500 A1 | 9/2006 | Klun et al. | |

FOREIGN PATENT DOCUMENTS

WO    WO 01/68384    9/2001

OTHER PUBLICATIONS

Mather, B.D., et al., "Michael addition reactions in macromolecular design for emerging technologies", *Prog. Polym. Sci.*, (2006) vol. 31, No. 5, pp. 487-531.
U.S. Appl. No. 11/277,162 entitled Perfluoropolyether Urethane Additives having (Meth)acryl Groups and Hardcoats filed Mar. 22, 2006.
U.S. Appl. No. 60/871,034 entitled "Fluorochemical Urethane Compounds Having Pendent Silyl Groups" filed Dec. 20, 2006.
U.S. Appl. No. 11/693,510 entitled "Michael-Adduct Fluorochemical Silanes" filed Mar. 29, 2007.
Kawashiro et al., "Gas Chromatography-Mass Spectrometry of N-Trifluoroacetyl Trimethysilyl Esters of Some Iminodicarboxylic Acids", Bull. Chem. Soc. Jpn., (Sep. 1985), pp. 2727-2728, vol. 58; No. 9, The Chemical Society of Japan.

* cited by examiner

*Primary Examiner*—Randy Gulakowski
*Assistant Examiner*—Robert Loewe
(74) *Attorney, Agent, or Firm*—Kent S. Kokko

(57) ABSTRACT

Fluorochemical silane compounds and coating compositions derived therefrom are described. The compounds and compositions may be used in treating substrates, in particular substrates having a hard surface such as ceramics or glass, to render them water, oil, stain, and soil repellent.

21 Claims, No Drawings

FLUOROCHEMICAL COMPOUNDS HAVING PENDENT SILYL GROUPS

FIELD OF THE INVENTION

The present invention relates to fluorochemical silane compounds and coating compositions derived therefrom, which may be used in treating substrates, in particular substrates having a hard surface such as ceramics or glass, to render them water, oil, stain, and soil repellent, and for treating antireflective substrates, such as optical lenses.

BACKGROUND

Although many fluorinated compositions are known in the art for treating substrates to render them oil and water repellent, there continues to be a desire to provide further improved compositions for the treatment of substrates, in particular substrates having a hard surface such as ceramics, glass and stone, in order to render them water-repellent, oil-repellent, and easy to clean. There is also a need for treating glass and plastic as a hard surface, particularly in the optical field, in order to render them stain, dirt and dust resistant. Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. Also, it is desired that the coatings show particularly good chemical and solvent resistance. The compositions should be conveniently be applied in an easy and safe way and are compatible with existing manufacturing methods. Preferably, the compositions will fit easily into the manufacturing processes that are practiced to produce the substrates to be treated.

SUMMARY

The present invention provides fluorochemical silane compounds of the formula formula

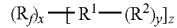

(1)

wherein $R_f$ is a fluorine-containing group;
$R^1$ is a covalent bond, a polyvalent alkylene or arylene group, or combinations thereof, said alkylene groups optionally containing one or more catenary oxygen or nitrogen atoms:
$R^2$ is a silane-containing group derived from the Michael reaction between an aminosilane and an acryloyl group;
x and y are each independently at least 1, and z is 1 or 2.

In one aspect, this invention relates to chemical compositions comprising one or more compounds and mixtures of compounds having at least one fluorine-containing group and at least one silane-containing moiety derived from the Michael reaction between an aminosilane and an acryloyl compound (such as an acrylated polyol having at least one fluorine-containing group).

Unless otherwise stated, the following terms used in the specification and claims have the meanings given below:

"Alkyl" means a linear or branched, cyclic or acylic, saturated monovalent hydrocarbon radical having from one to about twelve carbon atoms, e.g., methyl, ethyl, 1-propyl, 2-propyl, pentyl, and the like.

"Acryloyl" means an acrylate, thioacrylate or acrylamide.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, 1-naphthylethyl, and the like."

"Alkarylene" means an arylene group, with an alkyl groups attached.

"Arylene" means an polyvalent, aromatic radical, such as phenylene, naphthalene, etc.

"Cured chemical composition" means that the chemical composition is dried or solvent has evaporated from the chemical composition from ambient temperature or higher until dryness. The composition may further be crosslinked as result of siloxane bonds formed between the silane compounds.

"Nucleophilic fluorochemical compound" means a compound having one or two nucleophilic functional groups, such as a hydroxyl group or an amine group, and a perfluoroalkyl, perfluoroalkylene, perfluorooxyalkyl or perfluorooxyalkylene group, e.g. $CF_9SO_2N(CH_3)CH_2CH_2OH$, $C_4F_9CH_2CH_2OH$, $C_2F_5O(C_2F_4O)_3CF_2CONHC_2H_4OH$, c-$C_6F_{11}CH_2OH$, and the like.

"Electrophilic fluorochemical compound" means a compound having one or two electrophilic functional groups, such as an acid, acyl halide or ester, and a perfluoroalkyl, perfluoroalkylene, perfluorooxyalkyl or perfluorooxyalkylene group, e.g. $C_4F_9CH_2CH_2CO_2CH_3$, $C_4F_9CO_2H$, $C_2F_5O(C_2F_4O)_3CF_2COCl$, c-$C_6F_{11}CO_2H$, and the like.

"Hard substrate" means any rigid material that maintains its shape, e.g., glass, ceramic, concrete, natural stone, wood, metals, plastics, and the like.

"Oxyalkoxy" has essentially the meaning given above for alkoxy except that one or more oxygen atoms may be present in the alkyl chain and the total number of carbon atoms present may be up to 50, e.g. $CH_3CH_2OCH_2CH_2O$—, $C_4H_9OCH_2CH_2OCH_2CH_2O$—, $CH_3O(CH_2CH_2O)_{1-100}H$, and the like.

"Oxyalkyl" has essentially the meaning given above for alkyl except that one or more oxygen heteroatoms may be present in the alkyl chain, these heteroatoms being separated from each other by at least one carbon, e.g., $CH_3CH_2OCH_2CH_2$—, $CH_3CH_2OCH_2CH_2OCH(CH_3)CH_2$—, $C_4F_9CH_2OCH_2CH_2$—, and the like.

"Oxyalkylene" has essentially the meaning given above for alkylene except that one or more oxygen heteroatoms may be present in the alkylene chain, these heteroatoms being separated from each other by at least one carbon, e.g., —$CH_2OCH_2O$—, —$CH_2CH_2OCH_2CH_2$—, —$CH_2CH_2OCH_2CH_2CH_2$—, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like "Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. $CF_3CF_2OCF_2CF_2-$, $CF_3CF_2O(CF_2CF_2O)_3CF_2CF_2-$, $C_3F_7O(CF(CF_3)CF_2O)_sCF(CF_3)CF_2-$, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., $-CF_2OCF_2-$, or $-[CF_2-CF_2-O]_r-[CF(CF_3)-CF_2-O]_s-$; wherein r and s are (for example) integers of 1 to 50.

"Perfluorinated group" means an organic group wherein all or essentially all of the carbon bonded hydrogen atoms are replaced with fluorine atoms, e.g. perfluoroalkyl, perfluorooxyalkyl, and the like.

"Nucleophilic acryloyl compound" means an organic compound with at least one primary or secondary nucleophilic groups per molecule, and at least one acryloyl group, including acrylate and acrylamide groups.

"Michael addition" refers to an addition reaction wherein a nucleophile, such as an aminosilane undergoes 1,4 addition to an acryloyl group.

DETAILED DESCRIPTION

The present invention provides fluorochemical silane compounds of formula I, described supra.

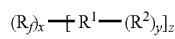

(I)

wherein $R_f$ is a fluorine-containing group, including a monovalent perfluoroalkyl-containing group or a perfluorooxyalkyl-containing group group, or a divalent perfluoroalkylene-containing group or a perfluorooxyalkylene-containing group;

$R^1$ is a covalent bond, a polyvalent alkylene or arylene group, or combinations thereof, said alkylene groups optionally containing one or more catenary oxygen or nitrogen atoms:

$R^2$ is a silane-containing group derived from the Michael reaction between and an aminosilane and an acryloyl group, $X^2$ is $-O-$, $-S-$ or $-NR_4-$, where $R^4$ is H or $C_1$-$C_4$ alkyl, $R^5$ is $C_1$-$C_4$ alkyl, or $-R^6-Si(Y_p)(R^7)_{3-p}$ or $(R_f)_x-R^1-X^2-C(O)-CH_2CH_2-$;

x and y are each independently at least 1, and z is 1 or 2.

With respect to Formula I, $R^2$ is derived by Michael addition of an aminosilane to an acryloyl group, as in the following formula:

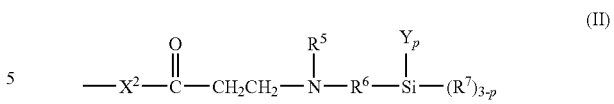

(II)

wherein $X^2$ is $-O-$, $-S-$ or $-NR^4-$, where $R_4$ is H or $C_1$-$C_4$ alkyl, $R^5$ is $C_1$-$C_4$ alkyl, or $-R^6-Si(Y_p)(R^7)_{3-p}$ or $(R_f)_x-R^1-X^2-C(O)-CH_2CH_2-$;

$R^6$ is a divalent alkylene group, said alkylene groups optionally containing one or more catenary oxygen or nitrogen atoms;

Y is a hydrolysable group, $R^7$ is a monovalent alkyl or aryl group, and p is 1, 2 or 3.

Although the inventors do not wish to be bound by theory, compounds of the above Formula I are believed to undergo a condensation reaction with the substrate surface to form a siloxane layer via hydrolysis or displacement of the hydrolysable "Y" groups of Formula II. In this context, "siloxane" refers to $-Si-O-Si-$ bonds to which are attached to compounds of Formula I. In the presence of water, the "Y" groups will undergo hydrolysis to "Si—OH" groups, and further condensation to siloxanes.

A coating prepared from the coating composition that includes compounds of Formula I includes the compounds per se, as well as siloxane derivatives resulting from bonding to the surface of a preselected substrate and intermolecular crosslinking by siloxane formation. The coatings can also include unreacted or uncondensed "Si—Y" groups. The composition may further contain non-silane materials such as oligomeric perfluorooxyalkyl monohydrides, starting materials and perfluorooxyalkyl alcohols and esters.

In one embodiment, the invention provides a coating composition comprising the compound of Formula I, a solvent, and optionally water and an acid. In another embodiment, the coating composition comprises an aqueous suspension or dispersion of the compounds of Formula I. To achieve good durability for many substrates, such as ceramics, the compositions of the present invention preferably include water. Thus the present invention provides a method of coating comprising the steps of contacting a substrate with a coating composition comprising the compounds of Formula I and a solvent. In another embodiment, compounds of Formula I may be applied by chemical vapor deposition methods to a substrate, particularly for antireflective substrates used in optical applications.

With respect to Formula I, the $R_f$ groups may comprise a monovalent perfluoroalkyl-containing group or a perfluorooxyalkyl-containing group, or a divalent perfluoroalkylene-containing group or a perfluorooxyalkylene-containing group. More particularly, $R_f$ may be represented by Formula III:

(III)

wherein $R_f^1$ is a monovalent perfluoroalkyl or a perfluorooxyalkyl group, or a divalent perfluoroalkylene or a perfluorooxyalkylene group.

Q can be a covalent bond, or a divalent linking group such as an alkylene, an arylene, an aralkylene, an alkarylene, Q can optionally include catenary heteroatoms such as O, N, and S, and combinations thereof. Q can also optionally include a heteroatom-containing functional group such as carbonyl or sulfonyl, and combinations thereof, such as sulfonamide, carboxamido, or ester, Q is further selected such that the "Q-CO—$X^2$—" moiety is not a carbamate, urea, or carbonate group; i.e. the atom adjacent the carbonyl is not a heteroatom;

$X^2$ is —O—, —$NR^4$— or —S—, where $R^4$ is H or $C_1$-$C_4$ alkyl, z is 1 or 2, and v is 0 or 1.

The $R_f^1$ groups of Formula III can contain straight chain, branched chain, or cyclic fluorochemical groups or any combination thereof. The $R_f^1$ groups can be mono- or divalent, and can optionally contain one or more catenary oxygen atoms in the carbon-carbon chain so as to form a carbon-oxygen-carbon chain (i.e. a perfluorooxyalkylene group). Fully-fluorinated groups are generally preferred, but hydrogen or other halo atoms can also be present as substituents, provided that no more than one atom of either is present for every two carbon atoms.

It is additionally preferred that any $R_f^1$ group contain at least about 40% fluorine by weight, more preferably at least about 50% fluorine by weight. The terminal portion of the monovalent $R_f^1$ group is generally fully-fluorinated, preferably containing at least three fluorine atoms, e.g., $CF_3$—, $CF_3CF_2$—, $CF_3CF_2CF_2$—, $(CF_3)_2N$—, $(CF_3)_2CF$—, $SF_5CF_2$—. In certain embodiments, monovalent perfluoroalkyl groups (i.e., those of the formula $C_nF_{2n+1}$—) or divalent perfluoroalkylene groups (i.e., those of the formula —$C_nF_{2n}$—) wherein n is 2 to 12 inclusive are the preferred $R_f^1$ groups, with n=3 to 5 being more preferred and with n=4 being the most preferred.

Useful perfluorooxyalkyl and perfluorooxyalkylene $R_f^1$ groups correspond to the formula:

$$W—R_f^3—O—R_f^4—(R_f^5)_q— \quad (IV)$$

wherein

W is F for monovalent perfluorooxyalkyl, and an open valence ("-") for divalent perfluorooxyalkylene $R_f^3$ represents a perfluoroalkylene group, $R_f^4$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group and q is 0 or 1. The perfluoroalkylene groups $R_f^3$ and $R_f^5$ in formula (IV) may be linear or branched and may comprise 1 to 10 carbon atoms, preferably 1 to 6 carbon atoms. A typical monovalent perfluoroalkyl group is $CF_3$—$CF_2$—$CF_2$— and a typical divalent perfluoroalkylene is —$CF_2$—$CF_2$—$CF_2$—, —$CF_2$— or —$CF(CF_3)CF_2$—. Examples of perfluoroalkyleneoxy groups $R_f^4$ include: —$CF_2$—$CF_2$—O—, —$CF(CF_3)$—$CF_2$—O—, —$CF_2$—$CF(CF_3)$—O—, —$CF_2$—$CF_2$—$CF_2$—O—, —$CF_2$—O—, —$CF(CF_3)$—O—, and —$CF_2$—$CF_2$—$CF_2$—$CF_2$—O—.

The perfluoroalkyleneoxy group $R_f^4$ may be comprised of the same perfluorooxyalkylene units or of a mixture of different perfluorooxyalkylene units. When the perfluorooxyalkylene group is composed of different perfluoroalkylene oxy units, they can be present in a random configuration, alternating configuration or they can be present as blocks. Typical examples of perfluorinated poly(oxyalkylene) groups include: —$[CF_2$—$CF_2$—O]_r$—; —$[CF(CF_3)$—$CF_2$—O]_s$—; —$[CF_2CF_2$—O]_r$—$[CF_2O]_t$—, —$[CF_2CF_2CF_2CF_2$—O]_u$ and —$[CF_2$—$CF_2$—O]_r$—$[CF(CF_3)$—$CF_2$—O]_s$—; wherein each of r, s, t and u each are integers of 1 to 50, preferably 2 to 25. A preferred perfluorooxyalkyl group that corresponds to formula (V) is $CF_3$—$CF_2$—$CF_2$—O—$[CF(CF_3)$—$CF_2O]_s$—$CF(CF_3)CF_2$— wherein s is an integer of 2 to 25.

Perfluorooxyalkyl and perfluoroxyalkylene compounds can be obtained by oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may then be reacted further to introduce the desired groups according to known procedures.

With respect to the $R_f$ group of Formula I or the $R_f^1$ group of Formula III, where y or z is 1, fluorochemical monofunctional compounds, preferably monoalcohols and monoamines are contemplated. Representative examples of useful fluorochemical monofunctional compounds include the following:

$CF_3(CF_2)_3SO_2N(CH_3)CH_2CH_2OH$, $CF_3(CF_2)_3SO_2N(CH_3)CH(CH_3)CH_2OH$, $CF_3(CF_2)_3SO_2N(CH_3)CH_2CH(CH_3)NH_2$, $CF_3(CF_2)_3SO_2N(CH_2CH_3)CH_2CH_2SH$, $CF_3(CF_2)_3SO_2N(CH_3)CH_2CH_2SCH_2CH_2OH$, $C_6F_{13}SO_2N(CH_3)(CH_{24}OH$, $CF_3(CF_2)_7SO_2N(H)(CH_2)_3OH$, $C_3F_7SO_2N(CH_3)CH_2CH_2OH$, $CF_3(CF_2)_4SO_2N(CH_3)(CH_2)_4NH_2$, $C_4F_9SO_2N(CH_3)(CH_2)_{11}OH$, $CF_3(CF_2)_5SO_2N(CH_2CH_3)CH_2CH_2OH$, $CF_3(CF_2)_5SO_2N(C_2H_5)(CH_2)_6OH$, $CF_3(CF_2)_2SO_2N(C_2H_5)(CH_2)_4OH$, $CF_3(CF_2)_3SO_2N(C_3H_7)CH_2OCH_2CH_2CH_2OH$, $CF_3(CF_2)_4SO_2N(CH_2CH_2CH_3)CH_2CH_2OH$, $CF_3(CF_2)_4SO_2N(CH_2CH_2CH_3)CH_2CH_2NHCH_3$, $CF_3(CF_2)_3SO_2N(C_4H_9)CH_2CH_2NH_2$, $CF_3(CF_2)_3SO_2N(C_4H_9)(CH_2)_4SH$, $CF_3(CF_2)_3CH_2CH_2OH$, $C_4F_9OC_2F_4OCF_2CH_2OCH_2CH_2OH$;

n-$C_6F_{13}CF(CF_3)CON(H)CH_2CH_2OH$; $C_6F_{13}CF(CF_3)CO_2C_2H_4CH(CH_3)OH$;

$C_3F_7CON(H)CH_2CH_2OH$; $C_3F_7O(CF(CF_3)CF_2O)_{1-36}CF(CF_3)CH_2OH$; and $C_3F_7O(CF(CF_3)CF_2O)_{1-36}CF(CF_3)C(O)N(H)CH_2CH_2OH$ and the like, and mixtures thereof.

With respect to the $R_f$ group of Formula I or the $R_f^1$ group of Formula III, where y or z is 2, fluorinated polyols and polyamines are contemplated. Representative examples of suitable fluorinated polyols include $R_f^1SO_2N(CH_2CH_2OH)_2$ such as N-bis(2-hydroxyethyl)perfluorobutylsulfonamide; $R_f^1OC_6H_4SO_2N(CH_2CH_2OH)_2$; $R_f^1SO_2N(R')CH_2CH(OH)CH_2OH$ such as $C_6F_{13}SO_2N(C_3H_7)CH_2CH(OH)CH_2OH$; $R_f^1CH_2CON(CH_2CH_2OH)_2$; $CF_3CF_2(OCF_2CF_2)_3OCF_2CON(CH_3)CH_2CH(OH)CH_2OH$; $R_f^1OCH_2CH(OH)CH_2OH$ such as $C_4F_9OCH_2CH(OH)CH_2OH$; $R^{f1}CH_2CH_2SC_3H_6OCH_2CH(OH)CH_2OH$; $R_f^1CH_2CH_2SC_3H_6CH(CH_2OH)_2$; $R_f^1CH_2CH_2SCH_2CH(OH)CH_2OH$; $R_f^1CH_2CH_2SCH(CH_2OH)CH_2CH_2OH$; $R_f^1CH_2CH_2CH_2SCH_2CH(OH)CH_2OH$ such as $C_5F_{11}(CH_2)_3SCH_2CH(OH)CH_2OH$; $R_f^1CH_2CH_2CH_2OCH_2CH(OH)CH_2OH$ such as $C_5F_{11}(CH_2)_3OCH_2CH(OH)CH_2OH$; $R_f^1CH_2CH_2CH_2OC_2H_4OCH_2CH(OH)CH_2OH$; $R_f^1CH_2CH_2(CH_3)OCH_2CH(OH)CH_2OH$; $R_f^1(CH_2)_4SC_3H_6CH(CH_2OH)CH_2OH$; $R_f^1(CH_2)_4SCH_2CH(CH_2OH)_2$; $R_f^1(CH_2)_4SC_3H_6OCH_2CH(OH)CH_2OH$; $R_f^1CH_2CH(C_4H_9)SCH_2CH(OH)CH_2OH$; $R_f^1CH_2OCH_2CH(OH)CH_2OH$;

$R_f^1CH_2CH(OH)CH_2SCH_2CH_2OH$; $R_f^1CH_2CH(OH)CH_2SCH_2CH_2OH$; $R_f^1CH_2CH(OH)CH_2OCH_2CH_2OH$; $R_f^1CH_2CH(OH)CH_2OH$; $R_f^1R''SCH(R'''OH)CH(R'''OH)SR''R_f$; $(R_f^1CH_2CH_2SCH_2CH_2SCH_2)_2C(CH_2OH)_2$; $[(CF_3)_2CFO(CF_2)_2(CH_2)_2SCH_2]_2C(CH_2OH)_2$; $(R_f^1R''SCH_2)_2C(CH_2OH)_2$; 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; 1,4-bis(1-hydroxy-1,1-dihydroperfluoropropoxy)perfluoro-n-butane $(HOCH_2CF_2CF_2O(CF_2)_4OCF_2CF_2CH_2OH)$; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); and perfluoropolyether diols such as Fomblin™ ZDOL $(HOCH_2CF_2O(CF_2O)_{8-12}(CF_2CF_2O)_{8-12}CF_2CH_2OH$, available from Solvay, Thorofore, N.J.); wherein $R_f$ is a perfluoroalkyl group having 1 to 12 carbon atoms, or a perfluorooxyalkyl group having 3 to about 50 carbon atoms with all perfluorocarbon chains present having 6 or fewer carbon atoms, or mixtures thereof, R' is alkyl of 1 to 4 carbon atoms; R'' is branched or straight chain alkylene of 1 to 12 carbon atoms, alkylenethio-alkylene of 2 to 12 carbon atoms, alkylene-oxyalkylene of 2 to 12 carbon atoms, or alkylene iminoalkylene of 2 to 12 carbon atoms, where the nitrogen atom contains as a third substituent hydrogen or alkyl of 1 to 6 carbon atoms; and R''' is a straight or branched chain alkylene of 1 to 12 carbon atoms or an alkylene-polyoxyalkylene of formula $C_rH_{2r}(OC_sH_{2s})_t$ where r is 1-12, s is 2-6, and t is 1-40.

Preferred fluorinated polyols include N-bis(2-hydroxyethyl)perfluorobutylsulfonamide; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); perfluoropolyether diols such as Fomblin™ ZDOL $(HOCH_2CF_2O(CF_2O)_{8-12}(CF_2CF_2O)_{8-12}CF_2CH_2OH)$, available from Solvay, Thorofore, N.J.); 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; and 1,4-bis(1-hydroxy-1,1-dihydroperfluoropropoxy)perfluoro-n-butane $(HOCH_2CF_2CF_2O(CF_2)_4OCF_2CF_2CH_2OH)$.

More preferred polyols comprised of at least one fluorine-containing group include N-bis(2-hydroxyethyl)perfluorobutylsulfonamide; 1,4-bis(1-hydroxy-1,1-dihydroperfluoropropoxy)perfluoro-n-butane $(HOCH_2CF_2CF_2O(CF_2)_4OCF_2CF_2CH_2OH)$ and $CF_3CF_2CF_2$—O—$[CF(CF_3)CF_2O]_n$-$CF(CF_3)$—, wherein n is an integer of 3 to 25. This perfluorinated polyether group can be derived from an oligomerization of hexafluoropropylene oxide. Such perfluorinated polyether groups are preferred in particular because of their benign environmental properties.

The $R^1$ moiety of Formula I between the $R_f$ group and the $R^2$ acryloyl group includes a polyvalent group selected from an alkylene, arylene, or combinations thereof and an optional catenary oxygen, or nitrogen heteroatom, or combinations thereof. $R^1$ can be unsubstituted or substituted with an alkyl, aryl, halo, or combinations thereof. The $R^1$ group typically has no more than 30 carbon atoms. In some compounds, the $R^1$ group has no more than 20 carbon atoms, no more than 10 carbon atoms, no more than 6 carbon atoms, or no more than 4 carbon atoms. For example, $R^1$ can be an alkylene, an alkylene substituted with an aryl group, or an alkylene in combination with an arylene.

The $R^1$ moiety of Formula I may be derived from an aliphatic or aromatic compound having at least two nucleophilic functional groups. Such compounds may be of the formula

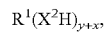

where $R^1$ is a covalent bond, a polyvalent alkylene or arylene group, or combinations thereof, said alkylene groups optionally containing one or more catenary oxygen or nitrogen atoms; each $X^2$ is independently —O—, —S—, or —NR$^4$—, where $R^4$ is H or $C_1$-$C_4$ alkyl, and x+y is at least two. Such compounds include polyols, polyamines, and hydroxyamines.

In one embodiment, the fluorochemical compounds of Formula I may comprise, in part, the reaction product of a fluorochemical compound having a mono- or difunctional perfluorinated group, and at least one electrophilic functional group; an electrophilic fluorochemical compound. Such compounds include those of the formula:

$$R_f^1\text{-}[Q\text{-}CO\text{—}X^3]_z, \qquad (V)$$

wherein $R_f^1$, Q, and z are as described for Formula III, and $X^3$ is —OH, a halogen atom, or OR$^4$, where $R^4$ is H or $C_1$-$C_4$ alkyl, or, i.e. the compounds of Formula V are esters, acids or acyl halides. Compounds of Formula V are particularly useful in the preparation of compounds or Formula I where $R^1$ is not a covalent bond, e.g. $R^1$ is the residue of a polyol, or polyamine.

The fluorochemical compounds of claim 1 may comprise, in part, the reaction product of a) a nucleophilic acryloyl compound of Formula VI (below) having a nucleophilic functional group and least one acryloyl group, and b) a compound of formula V (supra) having a fluorine-containing groups and an electrophilic group. The acryloyl moiety may be an acrylate or acrylamide, and the nucleophilic functional group may be an amino, thiol or hydroxy group. Preferably, the nucleophilic acryloyl compound is a polyacryl compound having a hydroxyl group and at least two acryloyl groups.

Such nucleophilic acryloyl compounds include those of the formula:

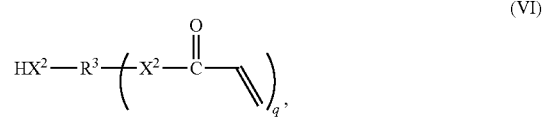

where
X is —O—, —S— or —NR$^4$—, preferably —O—, where $R^4$ is H or $C_1$-$C_4$ alkyl,
$R^3$ is a polyvalent alkylene or arylene groups, or combinations thereof, said alkylene groups optionally containing one or more catenary oxygen or nitrogen atoms; and q is 1 to 5. It will be understood that the terminal "HX$^2$" groups is preferably not —NR$^4$H, as a terminal amine may polymerize by Michael addition. Use of such terminal amine may require a protecting group to prevent such Michael polymerization until the acryloyl groups has been functionalized by the aminosilane.

Preferably q is greater than 1. The resulting multiple acryloyl groups allow the preparation of compounds of Formula I with multiple silane groups. The molar ratio of silane groups to $R_f$ groups may be greater than 1:1, or greater than 2:1.

Useful nucleophilic acryloyl compounds of Formula VI include, for example, acrylate compounds selected from the group consisting of (a) monoacryloyl containing compounds such as hydroxyethyl acrylate, glycerol monoacrylate 1,3-butylene glycol monoacrylate, 1,4-butanediol monoacrylate, 1,6-hexanediol monoacrylate, alkoxylated aliphatic monoacrylate, cyclohexane dimethanol monoacrylate, alkoxylated hexanediol monoacrylate, alkoxylated neopentyl glycol monoacrylate, caprolactone modified neopentylglycol hydroxypivalate acrylate, caprolactone modified neopentylglycol hydroxypivalate monoacrylate, diethylene glycol monoacrylate, dipropylene glycol monoacrylate, ethoxylated bisphenol-A monoacrylate, hydroxypivalaldehyde modified trimethylolpropane monoacrylate, neopentyl glycol monoacrylate, propoxylated neopentyl glycol monoacrylate, tetraethylene glycol monoacrylate, tricyclodecanedimethanol monoacrylate, triethylene glycol monoacrylate, tripropylene glycol monoacrylate; (b) multiacryloyl-containing compounds such as glycerol diacrylate, ethoxylated triacrylates (e.g., ethoxylated trimethylolpropane diiacrylate), pentaerythritol triacrylate, propoxylated diacrylates (e.g., propoxylated (3) glyceryl diacrylate, propoxylated (5.5) glyceryl diacrylate, propoxylated (3) trimethylolpropane diacrylate, propoxylated (6) trimethylolpropane diacrylate), trimethylolpropane diacrylate, higher functionality (meth)acryl containing compounds such as di-trimethylolpropane tetraacrylate, and dipentaerythritol pentaacrylate.

Such compounds are widely available from vendors such as, for example, Sartomer Company, Exton, Pa.; UCB Chemicals Corporation, Smyrna, Ga.; and Aldrich Chemical Company, Milwaukee, Wis. Additional useful acrylate materials include dihydroxyhydantoin moiety-containing polyacrylates, for example, as described in U.S. Pat. No. 4,262,072 (Wendling et al.).

With respect to the exemplary nucleophilic acryloyl compounds, it will be understood that the corresponding acrylamides and thioacrylates may be used. Further, the indicated hydroxyl groups may be substituted by the corresponding thiol group.

In another embodiment, the fluorochemical compound of Formula I may comprise, in part, the reaction product of a nucleophilic fluorochemical compound having a mono- or difunctional perfluorinated group, and at least one nucleophilic functional group; and a electrophilic acryloyl compound. Such nucleophilic fluorochemical compounds include those of the formula:

(VII) where $R_f^1$, Q, $X^2$, y and z are as described for Formula III. Compounds of Formula VII are particularly useful in the preparation of compounds of Formula I, where $R^1$ is a covalent bond, and may be functionalized with an acryloyl groups by reaction with an acryloyl halide, or functional equivalent.

Thus the compounds of Formula I may be prepared via an intermediate polyacryloyl compound of the formula

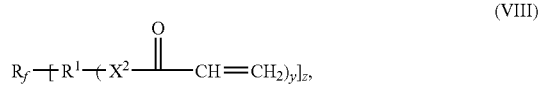

(VIII)

where
$R_f$, $R^1$, $X^2$, y and z are as previously described for Formula I.
Subsequently, the polyacryloyl compound of Formula VIII may be functionalized with a silane groups through Michael addition of an aminosilane.

Preferred aminosilanes may be represented by the general formula:

(IX)

wherein
$R^5$ is H, $C_1$-$C_4$ alkyl, or —$R^6$—$Si(Y_p)(R^7)_{3-p}$;
$R^6$ is a divalent alkylene group, said alkylene groups optionally containing one or more catenary oxygen atoms;
Y is a hydrolysable group,
$R^7$ is a monovalent alkyl or aryl group,
p is 1, 2 or 3, preferably 3.

It will be understood that in the presence of water, the Y groups may hydrolyze to —OH groups, leading to reaction with a substrate surface to form siloxane linkages Bonds thus formed, particularly Si—O—Si bonds, are water resistant and can provide enhanced durability of the stain-release properties imparted by the chemical compositions of the present invention.

With respect to the aminosilanes of Formula IX, it should be noted that primary amines, those where $R^5$ is H, are capable of reacting with two acryloyl groups by Michael addition, which may lead to crosslinking of the fluorochemical compounds of Formula I. Such compounds may be represented by Formula II where the $R^5$ group is $(R_f)_x$—$R^1$—$X^2$—C(O)—$CH_2CH_2$—.

Some aminosilanes useful in the practice of this invention are described in U.S. Pat. No. 4,378,250 (Treadway et al., incorporated herein by reference) and include aminoethyltriethoxysilane, β-aminoethyltrimethoxysilane, β-aminoethyltriethoxysilane, β-aminoethyltributoxysilane, β-aminoethyltripropoxysilane, α-amino-ethyltrimethoxysilane, α-aminoethyltriethoxysilane, γ-aminopropyltrimethoxysilane, γ-aminopropyltriethoxysilane, γ-aminopropyltributoxysilane, γ-aminopropyltripropoxysilane, β-aminopropyltrimethoxysilane, β-aminopropyltriethoxysilane, β-aminopropyltripropoxysilane, β-aminopropyltributoxysilane, α-aminopropyltrimethoxysilane, α-aminopropyltriethoxysilane, α-aminopropyltributoxysilane, and α-aminopropyltripropoxysilane, Minor amounts (<20 mole percent) of catenary nitrogen-containing aminosilanes may also be used, including those described in U.S. Pat. No. 4,378,250 (Treadway et al., incorporated herein by reference. N-(β-aminoethyl)-β-aminoethyltrimethoxysilane, N-(β-aminoethyl)-β-aminoethyltriethoxysilane, N-(β-aminoethyl)-β-aminoethyltripropoxysilane, N-(β-aminoethyl)-α-aminoethyltrimethoxysilane, N-(β-aminoethyl)-α-aminoethyltriethoxysilane, N-(β-aminoethyl)-α-aminoethyltripropoxysilane, N-(β-aminoethyl)-β-aminopropyltrimethoxysilane, N-(β-aminoethyl)-γ-aminopropyltriethoxysilane, N-(β-aminoethyl)-γ-aminopropyltripropoxysilane, N-(β-aminoethyl)-γ-aminopropyltrimethoxysilane, N-(β-aminoethyl)-β-aminopropyltriethoxysilane, N-(β-aminoethyl)-β-aminopropyltripropoxysilane, N-(γ-aminopropyl)-β-aminoethyltrimethoxysilane, N-(γ-aminopropyl)-β- aminoethyltriethoxysilane, N-(γ-aminopropyl)-β-aminoethyltripropoxysilane, N-methylaminopropyltrimethoxysilane, β-aminopropylmethyl diethoxysilane, and γ-diethylene triaminepropyltriethoxysilane.

The fluorochemical compounds of Formula I may be prepared in a three step process. The first step is by reaction of electrophilic fluorochemical compounds of Formula V, such as $C_4F_9C(O)OCH_3$, with compounds of the formula $R^1(X^2H)_{y+x}$ containing at least 2 nucleophilic groups, such as alcohol or primary or secondary amino groups to produce the corresponding fluorochemical amido-polyols or polyamines, ester-polyols or polyamines, or amides, or esters with mixed amine and alcohol groups. The second step is the acrylation of the remaining alcohol and/or amine groups (of $R^1(X^2H)_{y+x}$) with acryloyl halides, esters, anhydrides or acrylic acid to produce the intermediate of Formula VIII. The third step is then to effect Michael addition of an aminosilane to the pendent acryloyl groups. Preferably the compound of the formula $R^1(X^2H)_{y+x}$ is a primary amino polyol, having one primary amino groups and at least two hydroxy groups.

In general, the reactive components and a solvent are charged to a dry reaction vessel in immediate succession or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the IR.

The fluorinated compound of Formula V is used in an amount sufficient to react with an average of 5 to 50 mole percent of the available amine or alcohol functional groups of the compound $R^1(X^2H)_{y+x}$. Preferably, the compound of Formula V is used to react with an average of 10 to 30 mole percent of the groups. The remaining groups, an average of about 50 to 95 mole percent, preferably 70 to 90 mole percent is functionalized by the acryloyl compound such as an acrylic ester, followed by Michael addition of the aminosilane (IX), resulting in a compound having both pendent fluorochemical groups and pendent silane groups.

Alternatively to the three step process, a nucleophilic fluorochemical compound of Formula VII may be reacted with an acrylic ester (or equivalent), followed by Michael addition of the aminosilane (IX) to produce a compound of the following formula:

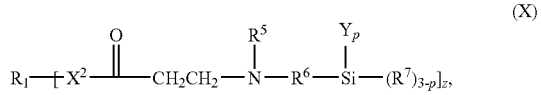

(X)

wherein $R_f$ is a fluorine-containing group;

$X^2$ is —O—, —S— or —NR$^4$—, where $R^4$ is H or $C_1$-$C_4$ alkyl, $R^5$ is $C_1$-$C_4$ alkyl, or —R$^6$—Si(Y$_p$)(R$^7$)$_{3-p}$ or (R$_f$)$_x$—X$^2$—C(O)—CH$_2$CH$_2$—;

$R^6$ is a divalent alkylene group, said alkylene groups optionally containing one or more catenary oxygen atoms;

Y is a hydrolysable group, $R^7$ is a monovalent alkyl or aryl group, p is 1, 2 or 3, and z is 1 or 2.

Alternatively, the aminosilane (IX) and the nucleophilic acryloyl compound (VI) may be pre-reacted, and then this Michael adduct of the following Formula XI is reacted with the fluorochemical of Formula V.

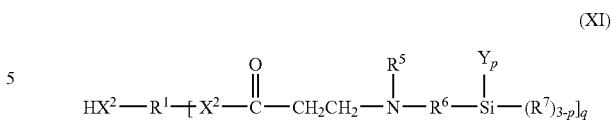

Where $R^1$, $R^5$, $R^6$, $R^7$, $X^2$, Y, p and q are as previously described for Formulas I and II.

Although no catalyst is generally required for the Michael addition of the aminosilanes to the acryloyl groups, suitable catalysts for the Michael reaction is a base of which the conjugated acid preferably has a pKa between 12 and 14. Most preferably used bases are organic. Examples of such bases are 1,4-dihydropyridines, methyl diphenylphosphane, methyl di-p-tolylphosphane, 2-allyl-N-alkyl imidazolines, tetra-t-butylammonium hydroxide, DBU (1,8-diazabicyclo[5.4.0]undec-7-ene) and DBN (1,5-diazabicyclo[4.3.0]non-5-ene), potassium methoxide, sodium methoxide, sodium hydroxide, and the like. A preferred catalyst in connection with this invention is DBU and tetramethylguanidine. The amount of catalyst used in the Michael addition reaction is preferably between 0.05% by weight and 2% by weight more preferably between 0.1% by weight and 1.0% by weight, relative to solids.

Compositions according to the present invention may be coated on a substrate and at least partially cured to provide a coated article. In some embodiments, the polymerized coating may form a protective coating that provides at least one of mar resistance, graffiti resistance, stain resistance, adhesive release, low refractive index, and water repellency. Coated articles according to the present invention include, for example, eyeglass lenses, mirrors, windows, adhesive release liners, and anti-graffiti films.

Suitable substrates include, for example, glass (e.g., windows and optical elements such as, for example, lenses and mirrors), ceramic (e.g., ceramic tile), cement, stone, painted surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form. The substrate may comprise a transparent or translucent display element, optionally having a ceramer hardcoat thereon.

In some embodiments, a coating composition comprising a mixture of the fluorochemical compounds and a solvent is provided. The coating compositions of the present invention comprise solvent suspensions, dispersions or solutions of the fluorochemical compounds of the present invention. When applied as coatings, the coating compositions impart oil- and water-repellency properties, and/or stain-release and stain-resistance characteristics to any of a wide variety of substrates.

The fluorochemical compounds can be dissolved, suspended, or dispersed in a variety of solvents to form coating compositions suitable for use in coating onto a substrate. Generally, the solvent solutions can contain from about 0.1 to about 50 percent, or even up to about 90 percent, by weight non-volatile solids (based on the total weight of the solid components). Coating compositions preferably contain from about 0.1 to about 10 weight percent fluorochemical silane compounds, based on the total solids. Preferably the amount of fluorochemical compounds used in the coating is about 0.1 to about 5 weight percent, most preferably from about 0.2 to about 1 weight percent, of the total solids. Suitable solvents include alcohols, esters, glycol ethers, amides, ketones, hydrocarbons, hydrofluorocarbons, hydrofluoroethers, chlorohydrocarbons, chlorocarbons, and mixtures thereof.

The coating composition may further comprise water and an acid. In one embodiment the method comprises contacting a substrate with a coating composition comprising the silane of Formula I and a solvent, and subsequently contacting the substrate with an aqueous acid.

For ease of manufacturing and for reasons of cost, the compositions of the present invention can be prepared shortly before use by diluting a concentrate of one or more of the compounds of Formula I. The concentrate will generally comprise a concentrated solution of the fluorochemical silane in an organic solvent. The concentrate should be stable for several weeks, preferably at least 1 month, more preferably at least 3 months. It has been found that the compounds can be readily dissolved in an organic solvent at high concentrations.

The coating compositions of this invention optionally contain silsesquioxanes or orthosilicates. The silsesquioxanes may be blended with the coating composition, or alternatively and coating of the compounds of Formula I may be coated on a previously applied coating of the silsesquioxanes. Useful silsesquioxanes include co-condensates of diorganooxysilanes (or hydrosylates thereof) of the formula $R^{10}_2Si(OR^{11})_2$ with organosilanes (or hydrosylates thereof) of the formula $R^{10}SiO_{3/2}$ where each $R^{10}$ is an alkyl group of 1 to 6 carbon atoms or an aryl group and $R^{11}$ represents an alkyl radical with 1 to 4 carbon atoms. Preferred silsesquioxanes are neutral or anionic silsesquioxanes, prior to addition to the composition. Useful silsesquioxanes can be made by the techniques described in U.S. Pat. No. 3,493,424 (Mohrlok et al.), U.S. Pat. No. 4,351,736 (Steinberger et al.), U.S. Pat. No. 5,073,442 (Knowlton et al.) U.S. Pat. No. 4,781,844 (Kortmann, et al), and U.S. Pat. No. 4,781,844, each incorporated herein by reference. Silsequioxanes may be added in amounts of 90 to 99.9 wt. % relative to the total solids.

The silsesquioxanes may be prepared by adding silanes to a mixture of water, a buffer, a surface active agent and optionally an organic solvent, while agitating the mixture under acidic or basic conditions. It is preferable to add the quantity of silane uniformly and slowly in order to achieve a narrow particle size of 200 to 500 Angstroms. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes, including tetralkoxysilanes and hydrosylates thereof (e.g. of the formula $Si(OH)_4$) present is less than 10 wt. %, preferably less than 5 wt. %, more preferably less than 2 wt. % relative to the weight of the silsesquioxane.

The following silanes are useful in preparing the silsesquioxanes of the present invention: methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, and 2-ethylbutoxytriethoxysilane.

The composition may be applied to the substrate by conventional techniques such as, for example, spraying, knife coating, notch coating, reverse roll coating, gravure coating, dip coating, bar coating, flood coating, dip coating or spin coating. The composition may be applied to any thickness to provide the desired level of water, oil, stain, and soil repellency. Typically, the composition is applied to the substrate as a relatively thin layer resulting in a dried cured layer having a thickness in a range of from about 40 nm to about 60 nm, although thinner and thicker (e.g., having a thickness up to 100 micrometers or more) layers may also be used. Next, any optional solvent is typically at least partially removed (e.g., using a forced air oven), and the composition is then at least partially cured to form a durable coating.

A preferred coating method for application of a fluorochemical silane of the present invention includes dip coating. A substrate to be coated can typically be contacted with the treating composition at room temperature (typically, about 20 to about 25° C.). Alternatively, the mixture can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

The present invention provides a protective coating on substrate that is relatively durable, and more resistant to contamination and easier to clean than the substrate surface itself. The present invention provides in one embodiment a method and composition for use in preparing a coated article comprising a substrate, preferably a hard substrate, and an antisoiling coating of greater than a monolayer (which is typically greater than about 15 Angstroms thick deposited thereon. Preferably an antisoiling coating of the present invention is at least about 20 Angstroms thick, and more preferably, at least about 30 Angstroms thick. Generally, the thickness of the coating is less than 10 micrometers, preferably less than 5 micrometers. The coating material is typically present in an amount that does not substantially change the appearance and optical characteristics of the article.

The compounds of claim 1 are particularly suited for preparing antisoiling coatings for antireflective substrates, such as those used in ophthalmic lenses. The coating can be provided by vapor deposition, or by dip-coating, flood coating, curtain coating, spin-coating, bar-coating or other solvent- or aqueous-borne methods.

Antireflective coatings may include one or more layers of material disposed on a transparent (i.e., light transmissive) substrate, such as glass, quartz, or organic polymeric substrates, including polymethyl methacrylate, polystyrene, polyvinyl chloride, polythiourethane, polyethylene, polypropylene, polycarbonate, polyimide, and polyesters, particularly polyethylene terephthalate. The simplest antireflective coating is a single layer of a transparent material having a refractive index less than that of the substrate on which it is disposed. Multilayer antireflective coatings include two or more layers of dielectric material on a substrate, wherein at least one layer has a refractive index higher than the refractive index of the substrate. They are often referred to as antireflective film stacks.

The antireflective coating may be provided by a wide variety of materials. Preferably, the antireflective coating is provided by a thin metal oxide film, and more preferably, by a thin sputter coated metal oxide film. Herein, "metal oxide" includes oxides of single metals (including metalloids) as well as oxides of metal alloys. Preferred metal oxides include silicon oxides, which may be depleted of oxygen (i.e., wherein the amount of oxygen in the oxide is less than the stoichiometric amount). Preferably, the metal oxide film on the outermost surface includes silicon oxides (SiOx, wherein x is no greater than 2), although other suitable materials include oxides of tin, titanium, niobium, zinc, zirconium, tantalum, yttrium, aluminum, cerium, tungsten, bismuth, indium, and mixtures thereof. Specific examples include $SiO_2$, $SnO_2$, $TiO_2$, $Nb_2O_5$, $ZnO$, $ZrO_2$, $Ta_2O_5$, $Y_2O_3$, $Al_2O_3$, $CeO_2$, $WO_3$, $Bi_2O$, $In_2O_3$, and ITO (indium tin oxide), as well combinations and alternating layers thereof.

Sputter coated metal oxide films are preferred over thermally evaporated films because sputter coated films have higher densities and are harder, smoother, and more stable than thermally evaporated films. Although such sputter coated metal oxide films are relatively porous and consist of clusters of particles with diameters on the order of about 5 nanometers to about 30 nanometers as measured by atomic force microscopy, they are sufficiently impermeable to water and gases that can alter their mechanical, electrical, and optical properties.

Suitable transparent substrates include glass and transparent thermoplastic materials such as poly(meth)acrylate, polycarbonate, polythiourethanes, polystyrene, styrene copolymers, such as acrylonitrile-butadiene-styrene copolymer and acrylonitrile-styrene copolymer, cellulose esters, particularly cellulose acetate and cellulose acetate-butyrate copolymer, polyvinyl chloride, polyolefins, such as polyethylene and polypropylene, polyimide, polyphenyleneoxide, and polyesters, particularly polyethylene terephthalate. The term "poly(meth)acrylate" (or "acrylic") includes materials commonly referred to as cast acrylic sheeting, stretched acrylic, poly(methylmethacrylate) "PMMA," poly(methacrylate), poly(acrylate), poly(methylmethacrylate-co-ethylacrylate), and the like. The substrate thickness can vary, however, for flexible organic films it typically ranges from about 0.1 mm to about 1 mm. Additionally, the organic polymeric substrate can be made by a variety of different methods. For example, the thermoplastic material can be extruded and then cut to the desired dimension. It can be molded to form the desired shape and dimensions. Also, it can be cell cast and subsequently heated and stretched to form the organic polymeric substrate.

The substrate on which the antireflective coating is deposited may include a primed surface. The primed surface can result from the application of a chemical primer layer, such as an acrylic layer, or from chemical etching, electronic beam irradiation, corona treatment, plasma etching, or coextrusion of adhesion promoting layers. Such primed substrates are commercially available. For example, a polyethylene terephthalate substrate primed with an aqueous acrylate latex is available from Imperial Chemical Industries Films, Hopewell, N.C.

Thus, the present invention provides an antisoiling composition for antireflective substrates, and method of depositing an antisoiling composition on an antireflective substrate comprising vaporizing an antisoiling composition and depositing the antisoiling composition onto an antireflective substrate. An antireflective substrate is any transparent substrate that is part of an antireflective film stack, or any transparent substrate having a surface that is covered in whole or in part with an antireflective composition. The antireflective composition is preferably an antireflective metal oxide, metal fluoride, metal nitride, metal sulfide, or the like. More preferably the antireflective composition is an antireflective metal oxide, and most preferably, the antireflective composition is a sputter coated antireflective metal oxide film (preferably comprising silicon oxides). An antisoiling composition of the present invention renders a surface more resistant to contamination, as by skin oils from fingerprints, for example. It also renders the surface easier to clean, preferably either with dry wiping or with water and detergent. Furthermore, it causes little or no disruption of the optical properties of the surface to which it is applied, particularly the antireflective surface of a film stack. That is, the antisoiling coating of the present invention does not significantly increase the reflectivity of the film stack.

The articles produced by the method of the present invention include a substrate, such as glass or an organic polymeric substrate, optionally having a primed surface on which is coated an optional adhesion enhancing coating, an antireflective composition, preferably, a multilayer film stack, and an antisoiling composition comprising the compounds of Formula I.

The overall thickness of the antisoiling composition results from balancing the desire for a thick coating for enhancing antisoiling and durability properties with the desire for a thin coating for maintaining the antireflective properties of the antireflective substrate. Typically, the overall coating thickness of an antisoiling composition of the present invention is from about 20 to 500 angstroms, more preferably from about 40 to 100 angstroms. In another aspect, the antisoiling composition is preferably deposited as a monolayer.

The conditions under which the antisoiling composition is vaporized may vary according to the structure and molecular weight of the antisoiling composition. In one aspect of the invention, it is preferred that the vaporizing may take place at pressures less than about 0.01 mmHg. In another aspect of the invention, the vaporizing may take place at temperatures of at least about 80° C.

In another embodiment of the present invention, the vaporizing comprises placing the antisoiling composition and the antireflective substrate into a chamber, heating the chamber (containing the antisoiling composition), and decreasing the pressure in the chamber, suing vapor deposition methods known in the art. The invention also provides a method wherein the chamber is heated prior to placing the antisoiling composition and antireflective substrate into the chamber. Alternatively, the antisoiling composition is placed in a first chamber and the antireflective coated ophthalmic lens is placed in a second chamber connected to the first chamber such that vaporized antisoiling composition from the first chamber can deposit on the antireflective coated ophthalmic lens in the second chamber. In another aspect of the invention, the second chamber may remain at ambient temperature while the first chamber is heated. Useful vacuum chambers and equipment are known in the art. One commercially available unit is the 900 DLS available from Satis Vacuum of America, Grove Port, Ohio.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, Milwaukee, Wis. unless otherwise noted.

17

Test Methods

Nuclear Magnetic Resonance (NMR)

$^1$H and $^{19}$F NMR spectra were run on a Varian UNITYplus 400 Fourier transform NMR spectrometer (available from Varian NMR Instruments, Palo Alto, Calif.).

IR Spectroscopy (IR)

IR spectra were run on a Thermo-Nicolet, Avatar 370 FTIR, obtainable from Thermo Electron Corporation, Waltham, Mass.

EXPERIMENTAL

Glossary List:

Unless otherwise noted, as used in the examples, "HFPO—" refers to the end group $F(CF(CF_3)CF_2O)_aCF(CF_3)$— of the methyl ester $F(CF(CF_3)CF_2O)_aCF(CF_3)C(O)OCH_3$, wherein a averages from 4-20, which can be prepared according to the method reported in U.S. Pat. No. 3,250,808 (Moore et al.), the disclosure of which is incorporated herein by reference, with purification by fractional distillation.

HFPO—C(O)N(H)CH$_2$CH$_2$OH was prepared by a procedure similar to that described in U.S. Pat. No. 7,094,829 (Audenart et al).

The HFPO dimethylester:

CH$_3$O(O)CCF(CF$_3$)(OCF$_2$CF(CF$_3$)$_b$OCF$_2$CF$_2$CF$_2$CF$_2$O(CF(CF$_3$)CF$_2$O)$_c$CF(CF$_3$)COOCH, also referred to as H$_3$CO(O)C—HFPO—C(O)OCH$_3$ or HFPO—(C(O)OCH$_3$)$_2$, in which b+c average from about 4 to 15 can be prepared using FC(O)CF$_2$CF$_2$C(O)F as an starting material according to the method reported in U.S. Pat. No. 3,250,807 (Fritz, et al.) which provides the HFPO oligomer bis-acid fluoride, followed by methanolysis and purification by removal of lower boiling materials by fractional distillation as described in U.S. Pat. No. 6,923,921 (Flynn, et. al.). HFPO—CONHCH$_2$CH$_2$OCOCH═CH$_2$ (HFPO-AEA) was prepared as described in Preparations 31A of U.S. 2006/0216500 (Klun et al.).

HFPO—CONHCH$_2$CH$_2$CH$_2$NHCH$_3$ was prepared according to the procedure given for (FC-1/AM-1) in US 2002/0250921).

C$_4$F$_9$CH$_2$CH$_2$OCOCH═CH$_2$ was purchased from Oakwood Products, Inc, West Columbia, S.C.

3-acryloxypropyltrimethoxysilane and Bis(trimethoxysilylpropyl)amine was obtained from Gelest, Inc. Morrisville, Pa.

The synthesis of material HFPO—CH$_2$OCOCH═CH$_2$ has been prepared by previously reported method (McIntyre, D. K. Patent: U.S. Pat. No. 4,873,140; Oct. 10, 1989)

NH$_2$CH$_2$CH$_2$—NH—CH$_2$CH$_2$—NH—CH$_2$CH$_2$—NH$_2$ was purchased from VWR international, Inc, West Chester, Pa.

LTM(CH$_2$OC(O)CH═CH$_2$)$_2$ is of the formula CH$_2$═CHC(O)OCH$_2$CF$_2$O(CF$_2$CF$_2$O)$_m$(CF$_2$O)$_n$CF$_2$CH$_2$OC(O)OCH═CH$_2$, and was prepared using a similar procedure as that of in U.S. Pat. No. 3,810,874, example XV, substituting acryloylchloride for methacryloyl chloride CH$_2$═CHC(O)O(CH$_2$)$_3$Si(OCH$_3$)$_3$ was purchased from VWR international, Inc, West Chester, Pa.

N-methyl Aminopropyltrimethoxy silane (MAPTMS) was obtained from Union Carbide Chemicals and Plastics Co. of Danbury, Conn.

Bis(propyl-3-trimethoxysilane)amine was obtained from Gelest, Morrisville, Pa.

18

Aminopropyltrimethoxy silane, (APTMS), was obtained from Sigma-Aldrich, Milwaukee, Wis.

Example 1

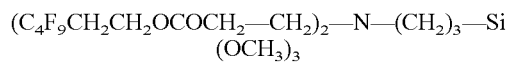

$(C_4F_9CH_2CH_2OCOCH_2—CH_2)_2—N—(CH_2)_3—Si(OCH_3)_3$

A 100 mL 3 necked round bottom flask was equipped with magnetic stir bar, N$_2$ inlet and reflux condenser was charged with C$_4$F$_9$CH$_2$CH$_2$OCOCH═CH$_2$ (5 g, 0.0157 moles) under N$_2$ atmosphere. 3-aminopropyltrimethoxysilane (1.40 g, 0.00785 moles) was added drop wise to the flask over a period of 15 minutes. The reaction was exothermic, and was stirred for 30 minutes at room temperature. After that the reaction mixture was heated at 55° C. for 12 h. The reaction was stopped after the complete disappearance of acrylate peaks monitored by $^1$H NMR.

Example 2

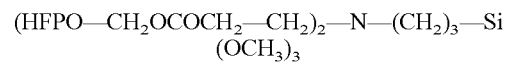

$(HFPO—CH_2OCOCH_2—CH_2)_2—N—(CH_2)_3—Si(OCH_3)_3$

A 100 mL 3 necked round bottom flask was equipped with magnetic stir bar, N$_2$ inlet and reflux condenser was charged with HFPO—CH$_2$OCOCH═CH$_2$ (5 g, 0.00395 moles) under N$_2$ atmosphere. 3-aminopropyltrimethoxysilane (0.35 g, 0.00197 moles) was added drop wise to the flask over a period of 15 minutes. The reaction was exothermic, and was stirred for 30 minutes at room temperature. After that the reaction mixture was heated at 55° C. for 12 h.

Example 3

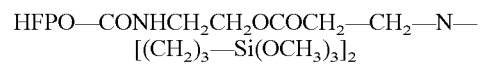

HFPO—CONHCH$_2$CH$_2$OCOCH$_2$—CH$_2$—N—[(CH$_2$)$_3$—Si(OCH$_3$)$_3$]$_2$

A 100 mL 3 necked round bottom flask was equipped with magnetic stir bar, N$_2$ inlet and reflux condenser was charged with HFPO—CONHCH$_2$CH$_2$OCOCH═CH$_2$ (10 g, 0.00714 moles under N$_2$ atmosphere. Bis(trimethoxysilylpropyl)amine (2.43 g, 0.00714 moles) was added dropwise to the flask over a period of 15 minutes. The reaction was exothermic, and was stirred for 30 minutes at room temperature. After that the reaction mixture was heated at 55° C. for 12 hrs.

Preparatory Example 1

Synthesis of HFPO—C(O)NHCH$_2$CH(OH)CH$_2$OH

A 500 mL 1 necked round bottom flask equipped with magnetic stir bar and inlet adapter was charged with HFPO—C(O)OCH$_3$ (MW: 1266, 64 g, 0.0506 moles) and (±)-3-Amino-1,2-propanediol (5.99 g, 0.06557 moles and stirred under nitrogen at 75° C. for 72 h. At this point, reaction was terminated as FTIR analysis confirmed the disappearance of a peak correlated with HFPO—C(O)OCH$_3$ (~1790 cm$^{-1}$) along with the appearance of a peak correlated with the desired amide (~1710 cm$^{-1}$). The product was dissolved in 70 g of Methyl tert-butyl ether and was stirred with 16 mL 2N (aq) HCl for 15 minutes at room temperature then placed in a separatory funnel to discard aqueous phase (pH=1). The organic phase was washed successively with three 100 g aliquots of water, discarding aqueous phase following separation each time, to achieve a neutral pH. Product was dried over 10 g magnesium sulfate and filtered on a Büchner funnel.

The organic layer was concentrated on a rotary evaporator at 65° C. and 28 torr). The $^1$H-NMR of HFPO—C(O)NHCH$_2$CH(OH)CH$_2$OH showed the desired product was free of excess (±)-3-Amino-1,2-propanediol.

Preparatory Example 2

Synthesis of HFPO—C(O)NHCH$_2$CH(OC(O)CH=CH$_2$)CH$_2$OC(O)CH=CH$_2$

A 500 ml 1 necked round bottom flask equipped with magnetic stir bar and inlet adapter was charged with HFPO—C(O)NHCH$_2$CH(OH)CH$_2$OH (MW: 1325, 60.88 g, 0.0459 moles, from preparatory example 1), Triethylamine (12.09 g, 0.1195 moles), methyl tert-butyl ether (82.95 g), and para-methoxyphenol (0.03 g, 500 PPM of solids) and stirred under dry air at 40° C. for 10 minutes. Acryloyl chloride (9.98 g, 0.1103 moles) was added drop wise to the flask over a period of fifteen minutes. The reaction was exothermic and was stirred for a period of 72 h. Product was then removed from heat and was stirred with 50 g 2N (aq) HCl for 20 minutes then placed in a separatory funnel to remove aqueous phase (pH=1). Product was then stirred with 90 g 10% (aq.) sodium carbonate for 20 minutes then placed in a separatory funnel to discard aqueous phase (pH=9). Product next stirred with 90 g 10% (aq) sodium chloride for 20 minutes then placed in a separatory funnel to discard aqueous phase. Product was dried over 10 g magnesium sulfate and filtered on a Büchner funnel. The organic layer was concentrated on a rotory evaporator (55° C., 28 torr). The $^1$H-NMR of HFPO—C(O)NHCH$_2$CH(OC(O)CH=CH$_2$)CH$_2$OC(O)CH=CH$_2$ was consistent with the desired product.

Example 4

HFPO—C(O)NHCH$_2$CH(OC(O)CH$_2$CH$_2$N(CH$_3$)(CH$_2$)$_3$Si(OCH$_3$)$_3$)CH$_2$OC(O)CH$_2$CH$_2$N(CH$_3$)(CH$_2$)$_3$Si(OCH$_3$)$_3$

A 500 ml 1 necked round bottom flask equipped with magnetic stir bar and inlet adapter was charged with HFPO—C(O)NHCH$_2$CH(OC(O)CH=CH$_2$)CH$_2$OC(O)CH=CH$_2$ (MW: 1433, 10 g, 0.0070 moles, from preparatory example 3) and stirred under dry air at 55° C. for 10 minutes. CH$_3$NH(CH$_2$)$_3$Si(OCH$_3$)$_3$ (MW: 193, 2.69 g, 0.0140 moles) was added drop wise to the flask over a period of fifteen minutes. The reaction was stirred for a period of 24 h. The $^1$H-NMR of HFPO—C(O)NHCH$_2$CH(OC(O)CH$_2$CH$_2$N(CH$_3$)(CH$_2$)$_3$Si(OCH$_3$)$_3$)CH$_2$OC(O)CH$_2$CH$_2$N(CH$_3$)(CH$_2$)$_3$Si(OCH$_3$)$_3$ was consistent with the desired product.

Example 5

HFPO—C(O)NHCH$_2$CH(OC(O)CH$_2$CH$_2$N((CH$_2$)$_3$Si(OCH$_3$)$_3$)$_2$)CH$_2$OC(O)CH$_2$CH$_2$N(CH$_3$)(CH$_2$)$_3$Si(OCH$_3$)$_3$)$_2$

A 500 ml 1 necked round bottom flask equipped with magnetic stir bar and inlet adapter was charged with HFPO—C(O)NHCH$_2$CH(OC(O)CH=CH$_2$)CH$_2$OC(O)CH=CH$_2$ (MW: 1433, 10 g, 0.0070 moles, from preparatory example 3) and stirred under dry air at 55° C. for 10 minutes. NH((CH$_2$)$_3$Si(OCH$_3$)$_3$)$_2$ (MW: 341, 4.76 g, 0.0140 moles) was added drop wise to the flask over a period of fifteen minutes. The reaction was stirred for a period of 24 h. The $^1$H-NMR of HFPO—C(O)NHCH$_2$CH(OC(O)CH$_2$CH$_2$N((CH$_2$)$_3$Si(OCH$_3$)$_3$)$_2$)CH2OC(O)CH$_2$CH$_2$N(CH$_3$)(CH$_2$)$_3$Si(OCH$_3$)$_3$)$_2$ was consistent with the desired product.

Example 6

LTM(CH$_2$OC(O)CH$_2$CH$_2$N((CH$_2$)$_3$Si(OCH$_3$)$_3$)$_2$)$_2$

A 100 mL 1 necked round bottom flask equipped with magnetic stir bar and inlet adapter was charged with LTM (CH$_2$OC(O)CH=CH$_2$)$_2$ (MW: 2142, 15 g, 0.0070 moles) and HN((CH$_2$)$_3$Si(OCH$_3$)$_3$)$_2$ (MW: 341, 4.78 g, 0.0140 moles) and was stirred under dry air at 65° C. for 24 h. The $^1$H-NMR of LTM(CH$_2$OC(O)CH$_2$CH$_2$N((CH$_2$)$_3$Si(OCH$_3$)$_3$)$_2$)$_2$ showed that the product was free of excess starting materials.

Example 7

LTM(CH$_2$OC(O)CH$_2$CH$_2$N(CH$_3$)(CH$_2$)$_3$Si(OCH$_3$)$_3$)$_2$

A 100 mL 1 necked round bottom flask equipped with magnetic stir bar and inlet adapter was charged with LTM (CH$_2$OC(O)CH=CH$_2$)$_2$ (MW: 2142, 15 g, 0.0070 moles) and HN(CH$_3$)(CH$_2$)$_3$Si(OCH$_3$)$_3$ (MW: 193.27, 2.71 g, 0.0140 moles) and was stirred under dry air at 55° C. for 24 h. The $^1$H-NMR of LTM(CH$_2$OC(O)CH$_2$CH$_2$N(CH$_3$)(CH$_2$)$_3$Si(OCH$_3$)$_3$)$_2$ showed that the product was free of excess starting materials.

Preparatory Example 3

Synthesis of HFPO—(C(O)NHCH$_2$CH$_2$OH)$_2$

A 500 mL 1 necked round bottom flask equipped with magnetic stir bar and inlet adapter was charged with HFPO—(C(O)OCH$_3$)$_2$ (MW: 2400, 150 g, 0.0625 moles) and ethanolamine (MW: 61.08, 9.93 g, 0.1625 moles) and stirred under nitrogen at 75° C. for 24 h. The reaction was terminated as FTIR analysis confirmed the disappearance of a peak correlated with HFPO—(C(O)OCH$_3$)$_2$ (~1790 cm$^{-1}$) along with the appearance of a peak correlated with the desired amide (~1710 cm$^{-1}$). The product was dissolved in 225 g of methyl tert-butyl ether and was stirred with 50 mL 2N (aq) HCl for 15 minutes at room temperature then placed in a separatory funnel to discard aqueous phase (pH=1). Product next stirred with 80 mL 2% (aq) sodium carbonate for 20 minutes then placed in a separatory funnel to discard aqueous phase (pH=8). Product next stirred with 50 mL 10% (aq) sodium chloride for 20 minutes then placed in a separatory funnel to discard aqueous phase. Product was dried over 10 g magnesium sulfate and filtered on a Büchner funnel. The organic layer was concentrated on a rotary evaporator (temperature: 55° C.; vacuum: 28 torr).

Preparatory Example 4

Synthesis of HFPO—(C(O)NHCH$_2$—CH$_2$—OC(O)CH=CH$_2$)$_2$

A 500 ml 1 necked round bottom flask equipped with magnetic stir bar and inlet adapter was charged with HFPO—(C(O)NHCH$_2$CH$_2$OH)$_2$ (MW: 2458, 50 g, 0.0203 moles), triethylamine (5.02 g, 0.0496 moles) and Fluorinert™ FC-77 (87.50 g, a petrfluorinated solvent available from the 3M Company) and stirred under dry air at 40° C. for 10 minutes. Acryloyl chloride (MW: 90.51, 4.42 g, 0.0488 moles) was added drop wise to the flask over a period of fifteen minutes. The reaction was exothermic and was stirred for a period of 24 h. The product was then removed from heat, stirred with 5 g water for 120 minutes then stirred with 5 g magnesium sulfate for 30 minutes and then stirred with 5 g 10% potassium carbonate for 30 minutes. Next, added 10 g silica gel and stirred for 60 minutes. Product was then filtered on a Büchner funnel which was then washed with additional Fluorinert FC77. The organic layer was concentrated on a rotary evaporator (temperature: 55° C.; vacuum: 28 torr). The $^{1}$H-NMR of HFPO—(C(O)NHCH$_2$CH$_2$OC(O)CH=CH$_2$)$_2$ was consistent with the desired product.

Example 8

HFPO—(C(O)NHCH$_2$CH$_2$OC(O)CH$_2$CH$_2$—N((CH$_2$)$_3$Si(OCH$_3$)$_3$)$_2$)$_2$ A 50 ml 1 necked round bottom flask equipped with magnetic stir bar and inlet adapter was charged with HFPO—(C(O)NHCH$_2$CH$_2$OC(O)CH=CH$_2$)$_2$ (MW: 2568, 9 g, 0.0035 moles, from preparatory example 4) and HN((CH$_2$)$_3$Si(OCH$_3$)$_3$)$_2$ (MW: 341, 2.39 g, 0.0070 moles) and stirred under dry air at 70° C. for 24 h.

Example 9

HFPO—(C(O)NHCH$_2$CH$_2$OC(O)CH$_2$CH$_2$—N(CH$_3$)(CH$_2$)$_3$Si(OCH$_3$)$_3$)$_2$

A 50 ml 1 necked round bottom flask equipped with magnetic stir bar and inlet adapter was charged with HFPO—(C(O)NHCH$_2$CH$_2$OC(O)CH=CH$_2$)$_2$ (MW: 2568, 9 g, 0.0035 moles, from preparatory example 4) and HN(CH$_3$)(CH$_2$)$_3$Si(OCH$_3$)$_3$ (MW: 193.27, 1.35 g, 0.0070 moles) and stirred under dry air at 70° C. for 24 h.

Preparatory Example 5

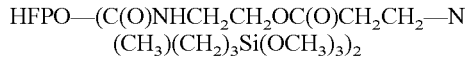
Synthesis of HFPO—C(O)NHCH$_2$CH$_2$N(CH$_3$)C(O)CH=CH$_2$

A 200 ml 1 necked round bottom flask equipped with magnetic stir bar and inlet adapter was charged with HFPO—C(O)NHCH$_2$CH$_2$CH$_2$NHCH$_3$ (MW: 1267.15, 25 g, 0.0197 moles), triethylamine (MW: 101.19, 2.60 g, 0.0256 moles), methyl-tert-butyl ether (29.74 g), and p-methoxyphenol (7.5 mg, 250 PPM) and stirred under dry air at 40° C. for 10 minutes. Acryloyl chloride (MW: 90.51, 2.14 g, 0.0237 moles) was added drop wise to the flask over a period of fifteen minutes. The reaction was exothermic and was stirred for a period of 24 h. The product was removed from heat, stirred with 15 mL 2N (aq) HCl for 15 minutes at room temperature, then placed in a separatory funnel to discard aqueous phase (pH=1). Product was then stirred with 100 mL water for 15 minutes at room temperature then placed in a separatory funnel to discard aqueous phase. This process was repeated three more times when the pH equaled 4. This product was dried over 5 g magnesium sulfate and filtered on a Büchner funnel. The organic layer was concentrated on a rotary evaporator (temperature: 55° C.; vacuum: 28 torr). The $^{1}$H-NMR of HFPO—C(O)NHCH$_2$CH$_2$CH$_2$N(CH$_3$)C(O)CH=CH$_2$ was consistent with the desired product.

Example 10

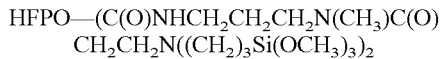
HFPO—(C(O)NHCH$_2$CH$_2$CH$_2$N(CH$_3$)C(O)CH$_2$CH$_2$N((CH$_2$)$_3$Si(OCH$_3$)$_3$)$_2$ A 50 ml 1 necked round bottom flask equipped with magnetic stir bar and inlet adapter was charged with HFPO—C(O)NHCH$_2$CH$_2$CH$_2$N(CH$_3$)C(O)CH=CH$_2$ (MW: 1322, 7 g, 0.0053 moles) and HN((CH$_2$)$_3$Si(OCH$_3$)$_3$)$_2$ (MW: 341, 1.90 g, 0.0056 moles) and stirred under dry air at 55° C. for 24 h. The $^{1}$H-NMR HFPO—C(O)NHCH$_2$CH$_2$CH$_2$N(CH$_3$)C(O)CH$_2$CH$_2$N((CH$_2$)$_3$Si(OCH$_3$)$_3$)$_2$ showed the desired product.

Example 11

(HFPO—C(O)NHCH$_2$CH$_2$OC(O)CH$_2$CH$_2$)$_2$N(CH$_2$)$_3$Si(OCH$_3$)$_3$ A 100 mL 3 necked round bottom flask was equipped with magnetic stir bar, N$_2$ inlet and reflux condenser was charged with HFPO—C(O)NHCH$_2$CH$_2$OC(O)CH=CH$_2$ (5 g, 0.00357 moles) under N$_2$ atmosphere. 3-aminopropyltrimethoxysilane (0.3203 g, 0.001786 moles) was added dropwise to the flask over a period of 15 minutes. The reaction was exothermic, and was stirred for 30 minutes at room temperature. After that the reaction mixture was heated at 55° C. for 12 h. A clear viscous oil obtained was analyzed by NMR.

Example 12

HFPO—C(O)NHCH$_2$CH$_2$OC(O)CH$_2$CH$_2$N(CH$_3$)(CH$_2$)$_3$Si(OCH$_3$)$_3$ A 100 mL 3 necked round bottom flask was equipped with magnetic stir bar, N$_2$ inlet and reflux condenser was charged with HFPO—CONHCH$_2$CH$_2$OCOCH=CH$_2$ (5 g, 0.00357 moles) under N$_2$ atmosphere. Next, 3-(methyl)aminopropyltrimethoxysilane (0.69 g, 0.00357 moles) was added dropwise to the flask over a period of 15 minutes. The reaction was exothermic, and was stirred for 30 minutes at room temperature. After that the reaction mixture was heated at 55° C. for 12 h. A clear viscous oil was obtained.

Treatment of Ophthalmic Lenses by Dip Coat

A 0.1% solution of the selected fluorochemical silane in Novec™ HFE-7100 (a hydrofluoroether available from the 3M Company) was placed in a glass container of the dip coater. The clean lens was dipped into the solution at the speed of 15 mm/sec and allowed to stay submerged for 2 seconds. Then the lens was withdrawn from the solution at the speed of 15 mm/sec. The coated lens was dried for 30 minutes in air and then dipped into 0.1% HCl solution at a similar dipping and withdrawal speed. Any excess acid was blown off with nitrogen gas. The lens was placed in an aluminum pan and cured in the oven for 30 minutes at 60° C.

Treatment of Ophthalmic Lenses by Chemical Vapor Deposition (CVD):

A clean lens was treated with each of selected fluorochemical silanes of this invention in a vapor deposition chamber under 3×10$^{-6}$ torr pressure. The vaporization temperature for the silanes ranged from 350-500° C. The coating was then cured under ambient conditions.

The polycarbonate AirWear Crizal™ anti-reflective lens blanks (obtained from Essilor USA, St. Petersburg, Fla.) are believed to have a scratch resistant hard coat, an antireflective (AR) coating and hydrophobic top coat. The AR coating is believed to comprise a four layer CVD coating comprising zirconium oxide/silicon oxide/zirconium oxide/silicon oxide.

To remove the hydrophobic topcoat, and allowed deposition of the fluorochemical silanes of the invention, the commercial lens blanks were rinsed with isopropanol and dried with an air blower, then exposed to vacuum plasma for 3 minutes in a Harrick PDC-32G Cleaner/Sterilizer (Harrick Scientific Corp. Pleasantville, N.Y.).

Drain Time Test:

For this test the drain time of a liquid from a treated ophthalmic lens was determined using a dip coater. The treated lenses are dipped into and subsequently withdrawn from a liquid (either oleic acid or isopropanol (IPA)). The withdrawal speed for the test was 5 cm (2 inches) per second. The time needed for the liquid to drain completely was measured with a timer.

Table 1 exhibit measured drain times for comparison of selected CVD and dip coated polycarbonate lenses for isopropanol and oleic acid. According to the data, in general, the CVD coating of the lenses results in shorter drain times for both IPA and oleic acid than the dip coating. Drain time is used to measure the slipperiness of a treated lens, the shorter the time needed for the liquid to drain completely, the more slippery of the surface. Faster draining of the liquid is also an indication of better hydrophobic an oleophobic surface.

Static and Dynamic Contact Angles:

The static, advancing and receding contact angle test provides a quick and precise prediction of the surface properties of coating materials. The contact angles for treated lenses (after drying and curing) were measured using a Kruss G120 and AST VCA 2500 XE Video Contact Angle System (AST Products, Inc.), both equipped with a computer for control and date process. The data was generated for both water and n-hexadecane. Table 2 summarizes the static, advancing and receding contact angles for lenses treated with various silanes using both CVD and dip coating processes. Measured contact angles were high for all treated lenses, although, in general, the lenses treated by dip coating resulted in slightly higher contact angles.

Hysteresis of Treated Lenses:

The difference between the maximum (advancing) and minimum (receding) contact angle values is called the contact angle hysteresis, which characterizes surface heterogeneity, roughness and mobility. It is possible that the easy cleaning performance of a coated surface is correlated to the contact angle hysteresis. The higher receding contact angle would help to remove the staining liquid from the treated surface. Thus, the smaller the contact angle hysteresis, the better the performance. The Table 1 lists the hysteresis of several treated lenses.

Durability Test:

The durability silane treatments on lenses were determined in the following manner: The treated lenses were subjected to an abrasion test using a Lens Eraser Abrasion Tester (obtained from Colts Laboratories, Inc., Clearwater, Fla.) and a 3M High Performance Cloth™ (Scotch-Brite™ Microfiber Dusting Cloth, obtained from 3M Company, St. Paul, Minn.) under a 2.27 kg (5 lbs.) load for 500 cycles. Then the contact angles for the treated lenses following the abrasion test were measured again using the method described above. Table 2 shows the contact angle data of the treated lenses after the abrasion resistance test. Table 3 shows the contact angle data for the lenses treated by dipcoat, before and after abrasion resistance test respectively.

Adhesion and Edging Testing:

This test is run to determine the ability of a pad to hold a lens in position in the edger during the cutting operation, which consists in machining the rim or periphery of the lens to conform it to the required dimensions of a frame. Sealing paper from one side of the Leap Pad III (available from the 3M Company, St Paul, Minn.) was peeled and applied to the center of the coated lens, which is firmly affixed in the torque tool with 30 cm (12¼") bar.

A block, the device that holds the lens in position while the lens rotates, was applied to the other side of the Leap Pad III. The torque tool with pad and lens was inserted into the edger (alignment of block flanges into blocker is critical) and firmly pressed with 2.86 atmospheres (42 psi) pressure on the pad. The tip of the torque tool was lined up with zero degree on the torque scale. A horizontal force of 0.45 kilogram (6 lbs) was applied using spring scale for one minute and the new position of torque tool on the torque scale was recorded as the degree from the zero position. If the torque degree is less than or equal to 5, it is considered to have adequate adhesion and ability to hold the lens in the edging process.

The test results for the silane treatments of this invention are shown in the Table 2. The torque degree for comparative Alize™ lens blank (obtained from Essilor USA) was >15, which requires a special temporary coating for the edging process (see WO 01/68384 and US2004/0253369). The new silane treatments described in this invention all pass this torque test. If the CVD coated lens of FC silanes was first washed with isopropanol before the torque test, the adhesion was improved and passed the test. Therefore, the silane treatments of this invention do not require a special temporary coating for the edging process.

TABLE 1

Contact angle Data for Michael adducts (Method Applied: CVD)

| | Initial Contact Angle | | | | | | | | | |
|---|---|---|---|---|---|---|---|---|---|---|
| | Static | | Advancing | | Receding | | Hysteresis | | Drain Time | |
| Example # | Water | Hexadecane | Water | Hexadecane | Water | Hexadecane | Water | Hexadecane | Oleic acid | IPA |
| 1 | 83 | 38 | 85.7 | 39.5 | 31.9 | 17.6 | 53.8 | 21.9 | 78.4 | 31.9 |
| 2 | 93.6 | 56.4 | 100.6 | 59.0 | 59.7 | 44.5 | 40.9 | 14.5 | 17.7 | 3.9 |
| 3 | 109.9 | 70.8 | 132.7 | 74.9 | 83.5 | 59.8 | 49.2 | 15.1 | 14.3 | 2.9 |
| 4 | 108.9 | 69.6 | 121.7 | 72.8 | 88.6 | 62.8 | 33.1 | 10 | 14.4 | 2.6 |
| 5 | 110.3 | 69.0 | 121.2 | 73.3 | 97.6 | 65.2 | 23.6 | 8.1 | 11.9 | 3.1 |
| 6 | 104.8 | 65.6 | 114.6 | 68.1 | 86.5 | 62.5 | 28.1 | 5.6 | 9.8 | 3.5 |
| 7 | 102.9 | 65.2 | 113.2 | 68.5 | 68.5 | 58.4 | 44.7 | 10.1 | 13.4 | 6.3 |
| 8 | 105 | 66.1 | 113.7 | 69.9 | 70.4 | 55.7 | 43.3 | 14.2 | 21.9 | 7.1 |
| 9 | 105.4 | 65.9 | 115.2 | 69.6 | 75.2 | 54.8 | 40 | 14.8 | 20.8 | 7.8 |
| 10 | 104.2 | 66.3 | 112.9 | 69.7 | 87.4 | 57.1 | 25.5 | 12.6 | 26.8 | 35.8 |

TABLE 2

Durability Data

| Example # | Contact angle after Durability test | | | | | | Edging Test |
|---|---|---|---|---|---|---|---|
| | Static | | Advancing | | Receding | | Leap Pad III |
| | Water | Hexa decane | Water | Hexa decane | Water | Hexa decane | Torque degree |
| 1 | | | | | | | 3 |
| 2 | 75.6 | 38.6 | 90.9 | 43.0 | 44.4 | 20.0 | 3 |
| 3 | 86.7 | 53 | 96.9 | 58.3 | 51.7 | 31.6 | 3 |
| 4 | 98.2 | 58.9 | 105.3 | 58.6 | 66.2 | 38.5 | 3 |
| 5 | 98.6 | 63.7 | 108.1 | 65.5 | 68.9 | 43.8 | 3 |
| 6 | 99.4 | 64.6 | 110 | 67.1 | 67.1 | 42.2 | 4 |
| 7 | 95.9 | 66.2 | 105.5 | 73.4 | 61.3 | 44.4 | 3 |
| 8 | 93.9 | 59.2 | 99.7 | 61.9 | 50 | 30.9 | |
| 9 | 88 | 55.1 | 97.8 | 58.3 | 46.9 | 30 | |
| 10 | 82 | 48 | 91.8 | 55.5 | 51 | 30.4 | |

TABLE 3

Contact angle Data for Michael adducts (Method Applied: Dipcoat)

| Example # | Initial Contact Angle/Contact Angle after Durability Test | | | | | |
|---|---|---|---|---|---|---|
| | Static | | Adv | | Rec | |
| | Water | Hexa Decane | Water | Hexa decane | Water | Hexa decane |
| 11 | 112/100 | 70/56 | 119/100 | 73/41 | 74/66 | 56 |

The invention claimed is:

1. A compound of the formula

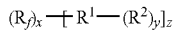

wherein $R_f$ is a fluorine-containing group of the formula:

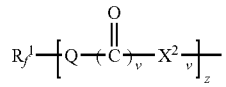

wherein
$R_f^1$ is a monovalent perfluorooxyalkyl group, or a divalent a perfluorooxyalkylene group comprising one or more perfluorinated repeating units selected from the group consisting of —$(C_nF_{2n}O)$—, —$(CF(Z)O)$—, —$(CF(Z)C_nF_{2n}O)$—, —$(C_nF_{2n}CF(Z)O)$—, —$(CF_2CF(Z)O)$—, and combinations thereof, wherein n is 1 to 4 and Z is a perfluoroalkyl group, a perfluoroalkoxy group, or perfluorooxyalkyl group, Q is a covalent bond, or a divalent alkylene or arylene group, said alkylene optionally containing one or more catenary heteroatoms, $X^2$ is —O—, —$NR^4$— or —S—, where $R^4$ is H or $C_1$-$C_4$ alkyl, z is 1 or 2, and v is 0 or 1;

$R^1$ is a covalent bond, a polyvalent alkylene or arylene group, or combinations thereof, said alkylene groups optionally containing one or more catenary oxygen or nitrogen atoms:

$R^2$ is of the formula:

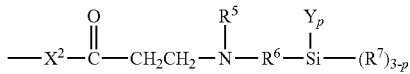

wherein
$X^2$ is —O—, —S— or —$NR^4$—, where $R^4$ is H or $C_1$-$C_4$ alkyl, $R^5$ is $C_1$-$C_4$ alkyl, or —$R^6$—Si$(Y_p)(R^7)_{3-p}$ or $(R_f)_x$—$R^1$—$X^2$—C(O)—$CH_2CH_2$—;

$R^6$ is a divalent alkylene group, said alkylene groups optionally containing one or more catenary oxygen atoms;

Y is a hydrolysable group, $R^7$ is a monovalent alkyl or aryl group, p is 1, 2 or 3, and x and y are each independently at least 1, and z is 1 or 2.

2. The compound of claim 1 wherein $R^2$ is a silane-containing moiety derived from a Michael reaction between a fluorine-containing acryloyl compound and an aminosilane.

3. The compound of claim 1 wherein $R_f^1$ comprises a group of the formula

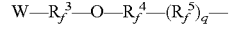

wherein
W is F for monovalent perfluorooxyalkyl, and an open valence ("—") for divalent perfluorooxyalkylene;

$R_f^3$ represents a perfluoroalkylene group, $R_f^4$ represents a perfluoroalkyleneoxy group consisting of perfluorooxyalkylene groups having 1, 2, 3 or 4 carbon atoms or a mixture of such perfluorooxyalkylene groups, $R_f^5$ represents a perfluoroalkylene group, and q is 0 or 1.

4. The compound of claim 1 wherein said perfluorooxyalkylene group is selected from one or more of —$[CF_2$—$CF_2$—$O]_r$—; —$[CF(CF_3)$—$CF_2$—$O]_s$—; —$[CF_2CF_2$—$O]_r$—, $[CF_2O]_t$—, —$[CF_2CF_2CF_2CF_2$—$O]_u$ and —$[CF_2$—$CF_2$—$O]_r$—$[CF(CF_3)$—$CF_2$—$O]_s$—; wherein each of r, s, t and u each are integers of 1 to 50.

5. The compound of claim 1 wherein $R_f^1$ is a monovalent perfluorooxyalkyl group and z is 1.

6. The compound of claim 1 wherein $R_f$ is derived from a fluorinated mono- or polyol.

7. The compound of claim 1, wherein Y is a halogen, a $C_1$-$C_4$ alkoxy group, or a $C_1$-$C_4$ acyloxy group.

8. The compound of claim 1 wherein the molar ratio of silane groups to $R_f$ groups is greater than 1:1.

9. The compound of claim 1 derived from a nucleophilic acryloyl compound of the formula

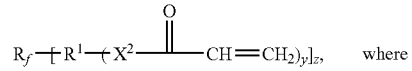

where $R_f$ is a fluorine-containing group;

$R^1$ is a covalent bond, a polyvalent alkylene or arylene group, or combinations thereof, said alkylene groups optionally containing one or more catenary oxygen or nitrogen atoms:

$X^2$ is —O—, —S— or —NR$^4$—, where R$^4$ is H or $C_1$-$C_4$ alkyl, y is at least 1, and z is 1 or 2.

10. The compound of claim 1, derived from an aminosilane is of the formula:

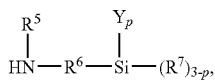

wherein

R$^5$ is $C_1$-$C_4$ alkyl, or —R$^6$—Si(Y$_p$)(R$^7$)$_{3-p}$;

R$^6$ is a divalent alkylene group, said alkylene groups optionally containing one or more catenary oxygen atoms;

Y is a hydrolysable group,

R$^7$ is a monovalent alkyl or aryl group, p is 1, 2 or 3, preferably 3.

11. A coating composition comprising at least one compound of claim 1 and a solvent.

12. The coating composition of claim 11 further comprising a silsesquioxane.

13. A method of coating comprising the step of contacting a substrate with the coating composition of claim 11.

14. A compound of claim 1 comprising a Michael addition reaction product of an aminosilane with a fluorine-containing compound having pendent acrylate groups; said fluorine-containing compound comprising the reaction product of an electrophilic fluorochemical compound, and a nucleophilic acryloyl compound.

15. A compound of claim 1 of the formula:

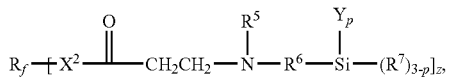

wherein

R$_f$ is a fluorine-containing group;

$X^2$ is —O—, —S— or —NR$^4$—, where R$^4$ is H or $C_1$-$C_4$ alkyl,

R$^5$ is $C_1$-$C_4$ alkyl, or —R$^6$—Si(Y$_p$)(R$^7$)$_{3-p}$ or (R$_f$)$_x$—X$^2$—C(O)—CH$_2$CH$_2$—;

R$^6$ is a divalent alkylene group, said alkylene groups optionally containing one or more catenary oxygen atoms;

Y is a hydrolysable group,

R$^7$ is a monovalent alkyl or aryl group, p is 1, 2 or 3, and z is 1 or 2.

16. A coated article comprising a substrate having a cured coating of the silane compounds of claim 1.

17. The coated article of claim 16 wherein the substrate is an antireflective substrate comprising an antireflective surface of a metal oxide film having one or more metal oxides.

18. The article of claim 17 wherein the antireflective surface comprises a vacuum deposited metal oxide film.

19. The article of claim 16, wherein the silane compounds are coated by vapor deposition.

20. The article of claim 16 comprising: a transparent substrate having a first surface and a second surface; an antireflective coating on at least a portion of the first surface; and a coating of the silane disposed on the antireflective coating.

21. The article of claim 20 wherein the transparent substrate comprises a flexible organic polymeric material.

* * * * *

UNITED STATES PATENT AND TRADEMARK OFFICE
CERTIFICATE OF CORRECTION

PATENT NO. : 7,745,653 B2
APPLICATION NO. : 11/683823
DATED : June 29, 2010
INVENTOR(S) : Suresh Subramaniya Iyer et al.

It is certified that error appears in the above-identified patent and that said Letters Patent is hereby corrected as shown below:

On the Title Pg, Item (56),
Under "Other Publications" line 12, delete "Trimethysilyl" and insert -- Trimethylsilyl --.

Column 1,
Line 42, after "formula" delete "formula".

Column 2,
Line 1, delete "acylic," and insert -- acyclic, --.

Column 3,
Line 8, after "like" insert -- . --.
Line 50, after "group" delete "group".

Column 4,
Line 10, delete "$R_4$" and insert -- $R^4$ --.
Line 17, delete "or3." and insert -- or 3. --.

Column 5,
Line 44, after "perfluorooxyalkylene" insert -- . --.

Column 6,
Line 7, delete "perfluoroxyalkylene" and insert -- perfluorooxyalkylene --.
Line 26, delete "$(CH_3)(CH_{24}OH,$" and insert -- $(CH_3)(CH_2)_4OH$, --.
Line 57, delete "$R^{f1}$" and insert -- $R_f^1$ --.

Column 7,
Line 1, delete "$R_f^1 CH2CH$" and insert -- $R_f^1 CH_2CH$ --.
Line 20, delete "Thorofore," and insert -- Thorofare, --.
Line 44, delete "Thorofore," and insert -- Thorofare, --.

Signed and Sealed this

Nineteenth Day of October, 2010

David J. Kappos
*Director of the United States Patent and Trademark Office*

CERTIFICATE OF CORRECTION (continued)
U.S. Pat. No. 7,745,653 B2

Column 8,
Line 55, delete "X" and insert -- $X^2$ --.

Column 9,
Line 23, delete "diiacrylate)," and insert -- diacrylate), --.

Column 11,
Lines 47-50, delete

" 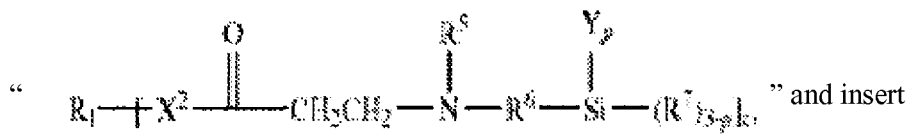 " and insert

-- 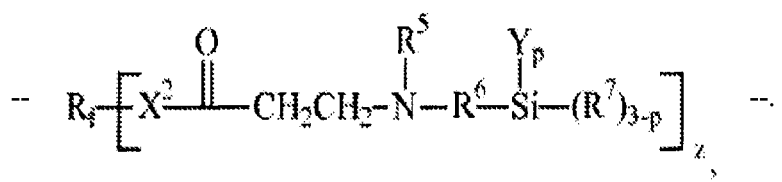 --.

Column 13,
Line 39, delete "Silsequioxanes" and insert -- Silsesquioxanes --.

Column 17,
Line 51, after "1989)" insert -- . --.
Line 60, after "chloride" insert -- . --.

Column 18,
Line 42, after "moles" insert -- ) --.

Column 19,
Line 29, delete "rotory" and insert -- rotary --.

Column 26,
Line 44, in Claim 4, delete

" $-[CF_2CF_2-O]_{r}-, [CF_2O]_{r'}-,$ " and insert

-- $-[CF_2CF_2-O]_{r}-[CF_2O]_{r'}-,$ --.

CERTIFICATE OF CORRECTION (continued)
U.S. Pat. No. 7,745,653 B2

Column 26,
Line 45, in Claim 4, delete " $-[CF_2-CF_2-O]_r-[CF(CF_3)-CF_2-O]_s-;$ " and insert -- $-[CF_2-CF_2-O]_r-[CF(CF_3)-CF_2-O]_s-;$ --.

Column 27,
Line 15, in Claim 10, delete " $-R^6-Si(Y_p)(R^7)_{3-p};$ " and insert -- $-R^6-Si(Y_p)(R^7)_{3-p};$ --.